United States Patent
Karerat et al.

(10) Patent No.: US 7,534,454 B2
(45) Date of Patent: May 19, 2009

(54) ANTI-CIGARETTE HERBAL FORMULATION AS AN ANTIDOTE TO TOBACCO

(76) Inventors: Arun Kumar Karerat, MIR Holistics Pvt. Ltd., c/o CSIR, Rafi Marg, New Delhi (IN) 110 002; Oommer Rowther Mohammed Ifthikar, MIR Holistics Pvt. Ltd., c/o CSIR, Rafi Marg, New Delhi (IN) 110 002; Joy Varghese, MIR Holistics Pvt. Ltd., c/o CSIR, Rafi Marg, New Delhi (IN) 110 002; Achuthan Venugopal Vellappillil, MIr Holistics Pvt. Ltd., c/o CSIR, Rafi Marg, New Delhi (IN) 110 002; Pushpangadan Palpu, c/o National Botanical Research Institute, Lucknow, Uttar Pradesh (IN); Ajay Kumar Singh Rawat, c/o National Botanical Research Institute, Lucknow, Uttar Pradesh (IN); Chandana Venkateswara Rao, c/o National Botanical Research Institute, Lucknow, Uttar Pradesh (IN); Raghavan Govindarajan, c/o National Botanical Research Institute, Lucknow, Uttar Pradesh (IN)

( * ) Notice: Subject to any disclaimer, the term of this patent is extended or adjusted under 35 U.S.C. 154(b) by 878 days.

(21) Appl. No.: 11/024,024

(22) Filed: Dec. 28, 2004

(65) Prior Publication Data

US 2006/0137702 A1    Jun. 29, 2006

(51) Int. Cl.
*A01N 65/00* (2009.01)
(52) U.S. Cl. .......................................... 424/725
(58) Field of Classification Search .................. None
See application file for complete search history.

(56) References Cited

FOREIGN PATENT DOCUMENTS

JP         10045542      *   2/1998

* cited by examiner

*Primary Examiner*—Michael V Meller
(74) *Attorney, Agent, or Firm*—Ladas and Parry LLP

(57) ABSTRACT

The present invention provides a novel nicotine free anticigarette herbal formulation as an anti-dote to the poisoning effects of tobacco products such as Cigarettes, Gutka, Pan masala and other similar tobacco related products. Formulation(s) comprises of sterilized dried plant powder/extracts together with the conventional additives to form the oral dosage forms, which include tablets, capsules, syrup and powders ready for suspension and mouth spray. The anti tobacco addiction herbal formulation comprises of *Sesbania grandiflora, Catharanthus roseus, Ocimum sanctum, Myristica fragrans, Elettaria cardamomum, Carum copticum, Syzygium aromaticum, Cinnamomum tamala, Acorus calamus, Zingiber officinale, Piper nigrum, Cinnamomum zeylanicum, Cuminum cyminum, Nigella sativum, Cinnamomum camphora, Piper longum Ocimum gratissimum* and *Hemidesmus indicus.*

61 Claims, 1 Drawing Sheet

ANTI-CIGARETTE HERBAL FORMULATION AS AN ANTIDOTE TO TOBACCO

FIELD OF THE INVENTION

The present invention relates to the development of anti-cigarette herbal nicotine free formulation as an antidote to tobacco.

BACKGROUND AND PRIOR ART OF THE INVENTION

The personal and societal habit of tobacco smoking has existed for centuries, but the severity of its potential detrimental health effects has undergone serious scrutiny only in the last few decades. It is now commonly accepted that tobacco smoke contains mutagenic and carcinogenic compounds that relate to serious adverse health consequences. The presence of these compounds in tobacco smoke creates a significant cost to society by increasing health costs and causing premature mortality. The adverse affects of tobacco smoke are linked to major pathological conditions such as: cancer, cardiovascular disease, stroke, chronic obstructive lung diseases (including chronic bronchitis, asthma and emphysema), periodontal disease etc. While recent efforts at educating consumers about the harmful effects of tobacco smoke and smoking prevention programs have been helpful, people continue to smoke despite these educational efforts to the contrary.

Attempts to reduce the harmful effects of tobacco smoke have included positioning filters of varying compositions within tobacco products. Current filters that are available, such as those made from cellulose acetate have only been moderately successful at decreasing the particulate portion of tobacco smoke that contains tar and nicotine. While reduction of tar mid nicotine are believed to be helpful, conventional filters have been unsuccessful at effectively removing components within the gas-vapor portion of tobacco smoke containing the most toxic components, with the exception of activated carbon filters which are known to remove small amounts of cyanide and carbon monoxide. Additionally, the relative health benefits of removing particulate matter and toxic components in the gas-vapor phase from tobacco smoke are not well understood and its effect on the health of smokers is without standards.

There have also been various proposed treatments for the administration of nicotine (the putative addictive substance in tobacco smoking) as a replacement for tobacco smoking. One of the most successful approaches, which have been used to date in reducing the incidence of tobacco smoking, relies upon nicotine containing chewing gum. The use of this type of gum suffers from several problems, including not only the bad taste and destruction of dental appliances, but the gastrointestinal upset which results there from and which also reduces compliance. Moreover, the nicotine containing chewing gums do not satisfy that craving which most smokers experience for the distinct sensations in the throat and chest elicited by the nicotine in smoke. Over the course of many years of tobacco smoking, these particular sensations have become an important part of and conditioned with the habit of smoking and help maintain tobacco smoke dependency.

There have also been several proposals for administering nicotine through various aerosol sprays. However, the aerosol sprays are designed to supply that amount of nicotine, which would have been acquired by a user through the normal channel of tobacco smoking. The sprays result in severe respiratory tract irritation. There is no available means to orally provide the nicotine either by means of an oral or nasal spray and attenuate the severe irritating effects of the nicotine.

Therefore there is an urgent need for a nicotine free antidote to tobacco smoking or addiction to tobacco related products. Hitherto, we provide a novel nicotine free herbal formulation as an anti-dote to the poisoning effects of tobacco products such as Cigarettes, Gutka, Pan masala and other similar tobacco products comprising of sterilized dried plant powder/extracts together with the conventional additives to form the oral dosage forms, which include tablets, capsules, syrup, powders ready for suspension and mouth spray.

OBJECTS OF THE INVENTION

The main object of the present invention is to provide a novel nicotine free herbal formulation as an antidote to poisoning effects of tobacco products such as Cigarettes, Gutka, Pan Masala and other similar tobacco products, comprising of sterilized dried plant powder/extracts together with conventional additives to form oral dosage forms, which include tablets, capsules, syrup, powders ready for suspension and mouth spray.

SUMMARY OF THE INVENTION

Accordingly, the present invention provides a herbal nicotine free pharmaceutical composition as an antidote to poisoning effects of tobacco, the composition comprising an effective amount of sterilized dried plant powder/extract obtained from *Sesbania grandiflora, Catharanthus roseus, Ocimum sanctum, Myristica fragrans, Elettaria cardamomum, Carum copticum, Syzygium aromaticum, Cinnamomum tamala, Acorus calamus, Zingiber officinale, Piper nigrum, Cinnamomum zeylanicum, Cuminum cyminum, Nigella sativum, Cinnamomum camphora, Piper longum, Ocimum gratssimum, Hemidesmus indicus.*

In one embodiment of the invention, the composition is admixed with pharmaceutically acceptable additives.

In another embodiment of the invention, the plant extracts are selected from powdered plant parts or lyophilized plant extracts *Sesbania grandiflora, Ocimum sanctum, Myristica fragrans, Elettaria cardamomum, Carum copticum, Syzygium aromaticum, Cinnamomum tamala, Acorus calamus, Zingiber officinale, Piper nigrum, Cinnamomum zeylanicum, Cuminum cyminum, Nigella sativum, Cinnamomum camphora, Piper longum, Ocimum gratssimum, Hemidesmus indicus* and *Catharanthus roseus.*

In another embodiment of the invention, the plant extracts are mixed in the following ratio: *Sesbania grandiflora* 15-20%, *Hemidesmus indicus* 1-2%, *Ocimum sanctum* 2-4%, *Myristica fragrans* 2-3%, *Elettaria cardamomum* 1-2%, *Carum copticum* 0.5-1%, *Syzygium aromaticum* 1-2%, *Cinnamomum tamala* 1-2%, *Acorus calamus* 0.5-1%, *Zingiber officinale* 1-2%, *Piper nigrum* 1-2%, *Cinnamomum zeylanicum* 1-2%, *Cuminum cyminum* 1-2%, *Nigella sativum* 1-2%, *Cinnamomum camphora* 0.2-0.5%, *Piper longum* 1-2%, *Ocimum gratissimum* 1-2% and *Catharanthus roseus* 10-15% and one or more additives to form an oral dosage form.

In another embodiment of the invention, the composition is nicotine free.

In another embodiment of the invention, the oral dosage form is selected from the group consisting of syrup, tablet, capsule, powder and spray.

In another embodiment of the invention, the extracts are aqueous alcoholic extracts.

In a further embodiment of the invention, the alcohol is ethanol.

In another embodiment of the invention, the composition comprises 15-50% wt. of total formulation.

In another embodiment of the invention, the plant powder/extract of *Sesbania grandiflora* is obtained from seeds or leaves.

In another embodiment of the invention, the plant powder/extract of *Catharanthus roseus* is obtained from leaves.

In another embodiment of the invention, the plant powder/extract of *Hemidesmus indicus* is obtained from stem.

In another embodiment of the invention, the plant powder/extract of *Ocimum sanctum* is obtained from leaves.

In another embodiment of the invention, the plant powder/extract of *Myristca fragrans* is obtained from fruits.

In another embodiment of the invention, the plant powder/extract of *Elettaria cardamomum* is obtained from fruits.

In another embodiment of the invention, the plant powder/extract of *Carum copticum* is obtained from fruits.

In another embodiment of the invention, the plant powder/extract of Syzygium aromaticum is obtained from flowers.

In another embodiment of the invention, the plant powder/extract of *Cinnamomum tamala* is obtained from leaves.

In another embodiment of the invention, the plant powder/extract of *Acorus calamus* is obtained from rhizomes.

In another embodiment of the invention, the plant powder/extract of *Zingiber officinale* is obtained from rhizome.

In another embodiment of the invention, the plant powder/extract of *Piper nigrum* is obtained from fruits.

In another embodiment of the invention, the plant powder/extract of *Cinnamomum zeylanicum* is obtained from bark.

In another embodiment of the invention, the plant powder/extract of *Cuminum cyminum* is obtained from fruit.

In another embodiment of the invention, the plant powder/extract of *Carum carvi* is obtained from fruit.

In another embodiment of the invention, the plant powder/extract of *Cinnamomum camphora* is obtained from bark or leaves.

In another embodiment of the invention, the plant powder/extract of *Piper longum* is obtained from fruit or roots.

In another embodiment of the invention, the plant powder/extract of *Ocimum gratissimum* is obtained from leaves.

In another embodiment of the invention, the additive used is a binder selected from the group consisting of starch, starch paste, gum acacia, carboxy methylcellulose, Talc (Purified), Magnesium Stearate, Sodium Methyl Paraben and Sodium Propyl Paraben.

In another embodiment of the invention, the additive is a diluent comprising lactose.

In another embodiment of the invention, the additive used is a lubricant selected from the group consisting of starch and lactose.

In another embodiment of the invention, the composition is mixed with a vehicle comprising 66.7% w/w sugar syrup.

In another embodiment of the invention, the composition acts as an antidote to the poisoning effects of tobacco and tobacco related products.

In another embodiment of the invention, the composition is effective in controlling complications associated with cigarette smoking.

In another embodiment of the invention, the composition is non-toxic and safe to use.

In another embodiment of the invention the composition reduces tobacco-induced toxicity.

In another embodiment of the invention, the composition maintains homeostasis in a subject administered with the formulation, provides supportive and protective cover to cellular and organic functions of heart, lungs, blood vessels, gastro-intestinal epithelium and mucosa.

In another embodiment of the invention, the composition acts as an antidote to slow and systemic poisoning experienced by tobacco smokers.

The present invention also relates to a method of preparing a herbal composition comprising an effective amount of sterilized dried plant powders/extracts obtained from *Sesbania grandiflora, Catharanthus roseus, Ocimum sanctum, Myristica fragrans, Elettaria cardamomum, Carum copticum, Syzygium aromaticum, Cinnamomum tamala, Acorus calamus, Zingiber officinale, Piper nigrum, Cinnamomum zeylanicum, Cuminum cyminum, Nigella sativum, Cinnamomum camphora, Piper longum, Ocimum gratssimum, Hemidesmus indicus* the method comprising:

(a) obtaining the part of medicinal plants from a group comprising leaves, root and aerial parts, rhizomes and any combination thereof;
(b) drying the plant material in shade;
(c) powdering the dried plant material to a coarse powder;
(d) sterilizing the plant powder;
(e) using the powder as such or extracting the powdered dried plant material with (40-50% aqueous ethanol) at 25-35° C.;
(f) extracting the plant materials with aqueous alcohol in a ratio of 1:8 to 1:15 for 4-7 days;
(g) concentrating the obtained extracts at under reduced pressure at 40-60° C.;
(h) lyophilising the concentrated extracts for complete removal of solvent.

In one embodiment of the invention, the composition is admixed with pharmaceutically acceptable additives.

In another embodiment of the invention, the plant extracts are selected from powdered plant parts or lyophilized plant extracts *Sesbania grandiflora, Ocimum sanctum, Myristica fragrans, Elettaria cardamomum, Carum copticum, Syzygium aromaticum, Cinnamomum tamala, Acorus calamus, Zingiber officinale, Piper nigrum, Cinnamomum zeylanicum, Cuminum cyminum, Nigella sativum, Cinnamomum camphora, Piper longum, Ocimum gratssimum, Hemidesmus indicus* and *Catharanthus roseus*.

In another embodiment of the invention, the plant extracts are mixed in the following ratio: *Sesbania grandiflora* 15-20%, *Hemidesmus indicus* 1-2%, *Ocimum sanctum* 2-4%, *Myristica fragrans* 2-3%, *Elettaria cardamomum* 1-2%, *Carum copticum* 0.5-1%, *Syzygium aromaticum* 1-2%, *Cinnamomum tamala* 1-2%, *Acorus calamus* 0.5-1%, *Zingiber officinale* 1-2%, *Piper nigrum* 1-2%, *Cinnamomum zeylanicum* 1-2%, *Cuminum cyminum* 1-2%, *Nigella sativum* 1-2%, *Cinnamomum camphora* 0.2-0.5%, *Piper longum* 1-2%, *Ocimum gratissimum* 1-2% and *Catharanthus roseus* 10-15% and one or more additives to form an oral dosage form.

In another embodiment of the invention, the composition is nicotine free.

In another embodiment of the invention, the oral dosage form is selected from the group consisting of syrup, tablet, capsule, powder and spray.

In another embodiment of the invention, the extracts are aqueous alcoholic extracts.

In a further embodiment of the invention, the alcohol is ethanol.

In another embodiment of the invention, the composition comprises 15-50% wt. of total formulation.

In another embodiment of the invention, the plant powder/extract of *Sesbania grandiflora* is obtained from seeds or leaves.

In another embodiment of the inventions the plant powder/extract of *Catharanthus roseus* is obtained from leaves.

In another embodiment of the invention, the plant powder/extract of *Hemidesmus indicus* is obtained from stem.

In another embodiment of the invention, the plant powder/extract of *Ocimum sanctum* is obtained from leaves.

In another embodiment of the invention, the plant powder/extract of *Myristca fragrans* is obtained from fruits.

In another embodiment of the invention, the plant powder/extract of *Elettaria cardamomum* is obtained from fruits.

In another embodiment of the invention, the plant powder/extract of *Carum copticum* is obtained from fruits.

In another embodiment of the invention, the plant powder/extract of *Syzygium aromaticum* is obtained from flowers.

In another embodiment of the invention, the plant powder/extract of *Cinnamomum tamala* is obtained from leaves.

In another embodiment of the invention, the plant powder/extract of *Acorus calamus* is obtained from rhizomes.

In another embodiment of the invention, the plant powder/extract of *Zingiber officinale* is obtained from rhizome.

In another embodiment of the invention, the plant powder/extract of *Piper nigrum* is obtained from fruits.

In another embodiment of the invention, the plant powder/extract of *Cinnamomum zeylanicum* is obtained from bark.

In another embodiment of the invention, the plant powder/extract of *Cuminum cyminum* is obtained from fruit.

In another embodiment of the invention the plant powder/extract of *Carum carvi* is obtained from fruit.

In another embodiment of the invention, the plant powder/extract of *Cinnamomum camphora* is obtained from bark or leaves.

In another embodiment of the invention, the plant powder/extract of *Piper longum* is obtained from fruit or roots.

In another embodiment of the invention, the plant powder/extract of *Ocimum gratissimum* is obtained from leaves.

In another embodiment of the invention, the additive used is a binder selected from the group consisting of starch, starch paste, gum acacia, carboxy methylcellulose, Talc (Purified), Magnesium Stearate, Sodium Methyl Paraben and Sodium Propyl Paraben.

In another embodiment of the invention, the additive is a diluent comprising lactose.

In another embodiment of the invention, the additive used is a lubricant selected from the group consisting of starch and lactose.

In another embodiment of the invention, the composition is mixed with a vehicle comprising 66.7% w/w sugar syrup.

The present invention also relates to a method for the amelioration of effect of tobacco and tobacco related products in a subject comprising administering to a subject a herbal composition comprising an effective amount of sterilized dried plant powders/extracts obtained from *Sesbania grandiflora, Catharanthus roseus, Ocimum sanctum, Myristica fragrans, Elettaria cardamomum, Carum copticum, Syzygium aromaticum, Cinnamomum tamala, Acorus calamus, Zingiber officinale, Piper nigrum, Cinnamomum zeylanicum, Cuminum cyminum, Nigella sativum, Cinnamomum camphora, Piper longum, Ocimum gratssimum Hemidesmus indicus*.

In one embodiment of the invention, the subject is a mammal.

In another embodiment of the invention, the mammal is a human being.

In another embodiment of the invention, the plant extracts are selected from powdered plant parts or lyophilized plant extracts *Sesbania grandiflora, Ocimum sanctum, Myristica fragrans, Elettaria cardamomum, Carum copticum, Syzygium aromaticum, Cinnamomum tamala, Acorus calamus, Zingiber officinale, Piper nigrum, Cinnamomum zeylanicum, Cuminum cyminum, Nigella sativum, Cinnamomum camphora, Piper longum, Ocimum gratssimum, Hemidesmus indicus* and *Catharanthus roseus*.

In another embodiment of the invention, the plant extracts are mixed in the following ratio: *Sesbania grandiflora* 15-20%, *Hemidesmus indicus* 1-2%, *Ocimum sanctum* 2-4%, *Myristica fragrans* 2-3%, *Elettaria cardamomum* 1-2%, *Carum copticum* 0.5-1%, *Syzygium aromaticum* 1-2%, *Cinnamomum tamala* 1-2%, *Acorus calamus* 0.5-1%, *Zingiber officinale* 1-2%, *Piper nigrum* 1-2%, *Cinnamomum zeylanicum* 1-2%, *Cuminum cyminum* 1-2%, *Nigella sativum* 1-2%, *Cinnamomum camphora* 0.2-0.5%, *Piper longum* 1-2%, *Ocimum gratissimum* 1-2% and *Catharanthus roseus* 10-15% and one or more additives to form an oral dosage form.

In another embodiment of the invention, the composition is nicotine free.

In another embodiment of the invention, the oral dosage form is selected from the group consisting of syrup, tablet, capsule, powder and spray.

In another embodiment of the invention, the composition is administered in a dosage of 1000 mg/kg of body weight or more without causing any biochemical changes in serum or change in organ weight of the subject or change in hematological parameters.

In another embodiment of the invention, the composition is administered in a dosage of 100-200 mg/kg of body weight and resulted in stoppage of smoking in 3-10 weeks treatment as well as showed free radical scavenging and anti-oxidant property.

DETAILED DESCRIPTION OF THE INVENTION

Figure 1:
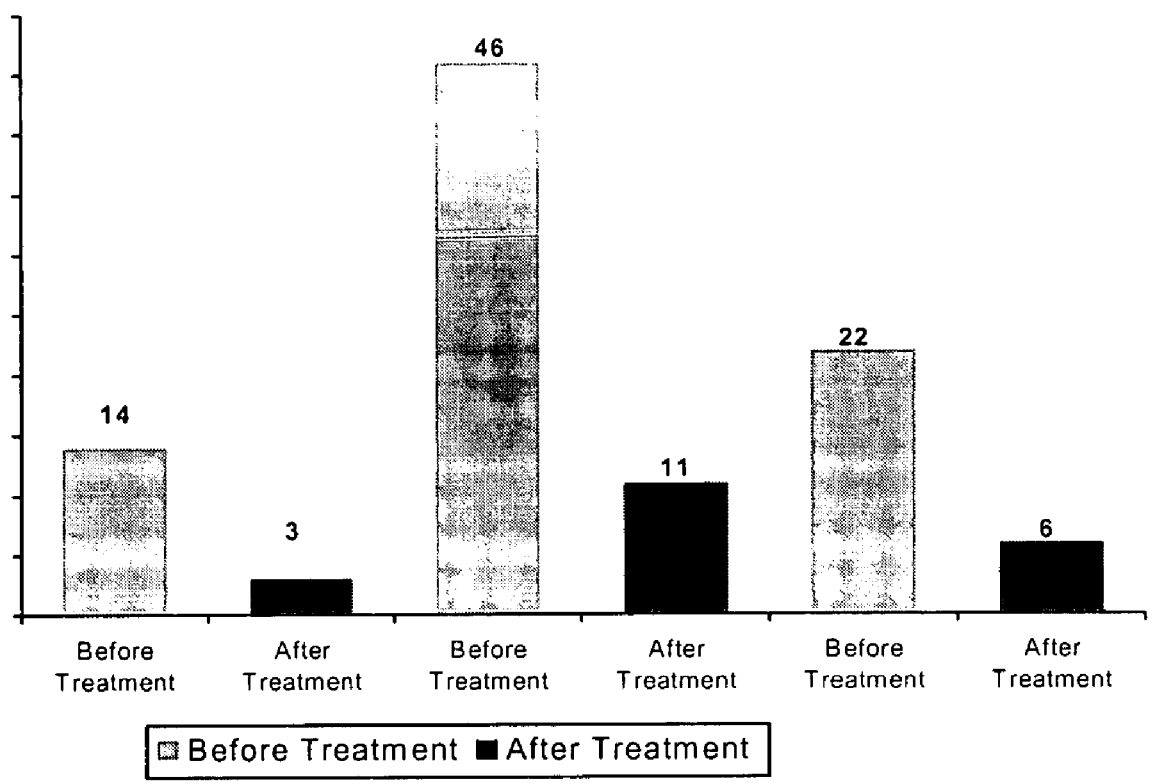
FIG. 1 shows the effect of anticigarette herbal formulation F2 on productive Cough.

The present invention provides a synergistic herbal nicotine free pharmaceutical composition as an antidote to the poisoning effects of tobacco and related products like cigarettes. The composition essentially comprises an effective amount of sterilized dried plant powder/extracts obtained from *Sesbania grandiflora, Catharanthus roseus, Ocimum sanctum, Myristica fragrans, Elettaria cardamomum, Carum copticum, Syzygium aromaticum, Cinnamomum tamala, Acorus calamus, Zingiber officinale, Piper nigrum, Cinnamomum zeylanicum, Cuminum cyminum, Nigella sativum, Cinnamomum camphora, Piper longum Ocimum gratssimum, Hemidesmus indicus*. If desired one or more pharmaceutical additives can be added and the composition converted to a solid dosage forms like tablet or capsule or used as a syrup, aerosol spray etc. *Sesbania grandiflora* and *Ocimum gratissimum* potentiated the free radical scavenging and 89.5% stopped smoking with the formulation containing the *Sesbania grandiflora* and *Ocimum gratissimum* than that of the composition containing the other components. The plants selected for developing the herbal formulation of the present invention as an antidote to tobacco are listed below:

*Acorus calamus* Family: Araceae

A semi-aquatic, perennial, aromatic herb with creeping rhizomes, growing wild and also cultivated throughout India, ascending to an altitude of 2,200 m in the Himalayas. Rhizome horizontal, jointed, somewhat vertically compressed, spongy within, 1.25-2.5 cm in thickness, pale to dark brown or occasionally orange-brown in colour: leaves grass-like or swored shaped, long and slender; flowers small, yellow-green in a spadix; berries green, angular, 1-3 seeded; seeds oblong.

Chemical constituents: The dry rhizomes contain 1.5 to 3.5% of a yellow aromatic volatile oil. It has a mellow odor resembling that of patchouli. The chief constituent of the oil is asaryl-aldehyde. There are also present a bitter glycoside named acorin and some other substances such as eugenol, ascarone, pinene and camphene. The Indian oil has much higher asarone content than the European commercial oil. Kelkar and Roe (1934) found that in addition to asarone, $C_{12}H_{16}O_3$ (mp 62 to 63° C.), the oil contains a small amount of sesquiterpenes and sequiterpenic alcohols. Fractionation of the active principle from volatile oil by gas phase chromatography revealed the presence of two components isolated in a pure state, i.e., α-asarone and β-asarone (Govindarajan et al., 2004), which were trans and cis isomers, respectively, of 2,4,5-trimethoxy-1-propenyl benzene. *Acorus* sp. is reported to contain an alkaloid choline (Williaman and Li, 1970).

Pharmacological action: The rhizome is an aromatic, stimulant, bitter, tonic, carminative, antispasmodic, emetic, expectorant, emmenagogue, aphrodisiac, laxative, and diuretic (Nandakarni, 1954). The alcoholic extract of the plant has been shown to possess sedative and analgesic properties; it causes a moderate depression in the blood pressure and respiration. The water-soluble fraction of the dealcoholized extract produced relaxation of isolated intestine and negative inotropic action on frog's heart. The insecticide activity of the solvent extracts and steam-distilled volatile principle of rhizome against common houseflies is quite marked. The insecticidal activity of the oil and the extract appears to be due to the presence of the trans-isomer of asarone (Agarwar et al, 1956).

Medicinal properties and uses: Its infusion is given in diarrhea, dysentery, bronchial and chest affections, and epilepsy. The burned root mixed with some bland oil is applied over the abdomen in flatulent colic; the poultice is also usefully applied to paralyzed limbs and rheumatic swelling. In Ayurvedic syste, of medicine, the rhizomes are considered to possess anti-spasmodic, carminative and anthelmintic properties and are used for the treatment of a host of disease such as epilepsy and other mental ailments, chronic diarrhoea and dysentery, bronchial catarrh, intermittent fevers and glandular and abdominal tumours.

*Cinnamomum camphora* Family: Lauraceae

A large, handsome, evergreen tree, native to China and Japan, introduced and cultivated in India as an ornamental and as a source of camphor; Leaves glabrous, chartaceous to sub-coriaceous, ovate-elliptic to elliptic to sub ovate elliptic, 3-10 cm×1-5 cm; panicles axillary, slender, glabrous, many flowered; fruits one seeded berries, globose, slightly fleshy, 5-10 mm in diameter, seated on a shallow, thin cup, turning black when ripe. *C. camphora* comprises many forms, some of them morphologically not differentiated but physiologically distinct. A few contain camphor while others produce only aromatic oil. The forms are distinguished based on principal chemical components like safrole, linalool, sesquiterpenes, camphor, caryophyllene, cineol, besides the physical constants of oil.

Chemical constituents: Camphor treated with chloride of zinc and distilled is converted into cymene, a substance contained in many essential oils. When it is treated with nitric acid it oxidizes and forms camphoric acid, a crystalline body, odorless and soluble in alcohol, ether and fatty oil. All parts of *C. camphora* on distillation yield semisolid oil from which camphor can be separated by a mechanical process. Seed fat contains glycerides of lauric, capric and oleic acid (Chopra et al., 1969).

Pharmacological action: Camphor is a local irritant with a benumbing influence upon the peripheral sensory nerve. Camphor is diaphoretic, stimulant, antiseptic, antispasmodic, internally expectorant, sedative, temporary aphrodisiac, narcotic, internally carminative and externally anodyne, carminative (Chopra et al., 1956).

Medicinal properties and uses: Camphor is esteemed as an analeptic in various cardiac depressions and has been used in the treatment of myocarditis. In doses of 0.2 g, it is very useful in hysteria and nervousness and is used in the treatment of serious diarrhoea. It is also employed in external application as an counterirritant in the treatment of muscular strains, rheumatic conditions, and inflammations. In combination with menthol or phenol it relieves itching of the skin. It is good in typhus, confluent smallpox, and all fevers and eruptions of the typhoid class; also in febrile delirium, whooping cough, hiccup, spasmodic asthma, dysmenorrhea, puerperal mania, cholera, epilepsy, atonic gout, melancholia, toothache and chronic bronchitis. In uterine pains, the liniment of camphor is rubbed on the abdomen.

*Cinnamomum tamala* Family: Lauraceae

A medium-sized tree, 7.5 m in height and 1.35 m in girth, distributed in tropical and sub-tropical Himalayas at altitudes of 1,002-2,400 m, in Khasi and Jaintia hills in Meghalaya at altitudes of 1,000-1,800 m, in Sikkim, Assam and Mizoram, and found cultivated in Tripura. Bark dark brown; leaves opposite or sometimes alternate, elliptic to oblong-lanceolate, glabrous, 3-nerved at base, pink when young; flowers pale yellow, pubescent, in panicles; fruits black, ovoid, in the thickened peduncle and enlarged base of the perianth. The plant are raised from seeds sown in nursery beds in March-April, Seedlings appear 30-45 days after sowing and are transplanted when 4-5 years old in the field at a spacing of 3 m×2 m. Sufficient shade is provided in the early stages of growth, and shade trees are cleared after 8-9 years. The fields are not usually manured; under-growth is occasionally removed.

Chemical constituents: The leaves yield an essential oil soluble in 1.2 vol of 70% alcohol. Oil resembles cinnamon leaf oil and contains d-α-phellandrene and 78% eugenol (Chopra et al., 1956). The essential oil from the bark is pale yellow and contains 70 to 85% aldehyde.

Pharmacological action: Carminative, stimulant, diuretic, diaphoretic, deobstruent, and lactagogue. Oil is a powerful stimulant (Kapoor L D, 2001).

Medicinal properties and uses: It is used for anorexia, bladder disorders, dryness of mouth, coryza, diarrhoea, nausea, and spermatorrhea. The bark in form of infusion, decoction, or powder is prescribed in bowl complaints such as dyspepsia, flatulence, and vomiting.

*Cinnamomum zeylanicum* Family: Lauraceae

A moderate sized tree, up to 16 m in height, native to Sri Lanka and cultivated in South India for its aromatic bark. The tree is also found to a limited extent in eastern India. Bark smooth, light pinkish brown, thin; live bark brown, up to 10 mm in thickness, with a strong, pleasant smell and spicy, burning taste; leaves opposite or sub-opposite, glabrous, thinly to stiffly coriaceous, oval or elliptic to lanceolate-oval or narrowly ellipsoid to oblong-ovoid, dark purple, up to 12.5 mm long.

Chemical constituents: Cinnamon bark oil contains cinnamaldehyde (60 to 75%): eugenol, benzaldehyde, methyl amyl ketone, phellandrene; pinene, cymene, nonyl aldehyde, linalool cumic aldehyde, carophyllene, and ester of isobutyric acid (Thorpe, 1950). The British Pharmacopoeia prescribed 50 to 65% cinnamic aldehyde content. Green leaves yield dark-colored oil on distillation, which differs from cinnamon bark oil. It contains 70 to 80% of eugenol with traces of cinnamic aldehyde, pinene, and linalool.

Pharmacological action: Bark is carminative, antispasmodic, aromatic, stimulant, hemostatic, astringent, antiseptic, stomachic, and germicide. Oil is a vascular and nervine stimulant; in large doses it is an irritant and narcotic poison (Kapoor L D, 2001).

Medicinal properties and uses: Infusion, decoction, or powder of bark is effective in bowel complaints such as dyspepsia, flatulency, diarrhoea, and vomiting. It is frequently employed as an adjunct to bitter tonic and purgatives. As a stimulant of uterine muscular fiber it is employed in menorrhagia and protracted labor due to defective uterine contractions. Crystalline cinnamic acid is antitubercular and is used as injection in phthisis (Mitra and Prasad, 1941).

*Myristica fragrans* Family: Myristicaceae

Dioecious or occasionally monoecious evergreen, aromatic tree, usually 9-12 m. high, but sometimes reaching a height of 20 m. or more. Bark grayish black, longitudinally fissured in old trees; leaves elliptic or oblong-lanceolate, coriaceous; flowers in umbellate cymes, creamy yellow, fragrant; fruits yellow, broadly pyriform or globose, 6-9, cm. Long, glabrous, often drooping: pericarp fleshy, 1.25 cm, thick, splitting in to 2 halves at maturity; seed broadly ovoid, arillate, albuminous, with a shell-like purplish brown testa; aril red, fleshy laciniate.

Chemical constituents: Nutmegs yield 5 to 15% of a volatile oil and also 30 to 405 of fat, photosterin, starch, amylodextrin, coloring matter, and a saponin (Trease and Evans, 1983). They yield about 3% of total ash and about 0.2% of acid-insoluble ash. Essential oil of mace is of a yellowish color with the odor of mace, and consists of macene. Mace (arillus) contains a volatile oil (8 to 17%), a fixed oil, resin, fat, sugar, destrin, and mucilage. The volatile oil (Oleum myristicae, British Pharmacopoeia) contains pinene and camphene (80%), dipentene (8%), alcohols (about 6%), myristicin (about 4%), safrole (0.6%), and eugenol and isoeugenol (0.2%). By expression or by means of solvents, nutmegs yield a product known as "nutmeg butter" or expressed oil of nutmegs. This consists of 12.5% of volatile oil, 73% of trimyristicin (the glyceride of myristic acid), small quantities of oleic, linoleic, and other acids, and about 8.5% of unsaponifiable matter (Chopra et al., 1982). Varshney and Sharma (1968) found triterpenic saponin and 15% of free myristic acid in the seeds of *M. fragrans*. The arils yield a new neolignan, characterized as dl-dehydro-di-isoeugenol, and five other neolignans (Purushottaman and Sharda 1980), Raw nutmeg contained 1.5% of total polyphenols and 0.6% tannins. The extract of nutmeg revealed the presence of epicatechin and cyaniding (Gopalakrishnan and Mathew, 1983). Nutmeg is also reported to contain calcium, phosphorus, iron, thiamin, riboflavin and niacin (Gopalan et al., 1948)

Pharmacological action: Nutmeg is aromatic, stimulant, and carminative; in large doses, narcotic. Mace is carminative and aphrodisiac. The extract of the seed and essential oil showed antibacterial activity. The seed oil exhibited a depressent effect on isolated frog rectus and a direct relaxant effect on rat ileum (Kapoor 2001).

Medicinal properties and uses: Essential oil is administered in atonic diarrhea and dysentery to relieve pain and is used in combination without stimulating oils for a stimulant action and in plasters for chronic rheumatism. A compound powder called Jatiphaladi churna made of nutmeg, Indian hemp, camphor, cardamon, cloves, bamboo manna and *Plumbago zeylanica* is used as a sedative, anodyne antispasmodic in asthma, colic, neualgia, menorrhagia, dysmenorrhea, spasmodic cough, and lumbago, in doses of 1 to 1.5 gr twice daily with honey. Mace is useful in low stages of fever, in consumptive complaints, and humoral asthma Roasted nutmeg is useful in obstructions of the liver and spleen.

*Zingiber officinale* Family: Zingiberaceae

A herbaceous, rhizomatous perennial, reaching up to 90 cm. in height under cultivation. Rhizomes are aromatic, thick-lobed, pale yellowish, differing in shape and size in the different cultivated types. The herb develops several lateral shoots in clumps which begin to dry when the plant matures; Leaves narrow, distichous sub-sessile, linear-lanceolate, 17 cm.×1.8 cm., dark green, evenly narrowed to form a slender tip; flowers in spikes, greenish yellow with a small dark purple or purplish black tip.

Chemical constituents: Indian ginger contains 1 to 2% volatile oil of yellow colour, with a characteristic odor and containing camphene, phellandrene, zingiberine, cineol and borneol; gingerol, a yellow pungent liquid; an oleoresin "gingerin" the active principle, resin, starch, and K oxalate. Pungency of gingerol and ginger is destroyed when boiled with 2% KOH.

Pharmacological action: Aromatic, carminative, stimulant to the gastrointestinal tract and stomachic; also sialgoge and digestive. Extermally a local stimulant and rubefacient.

Medicinal properties and uses: Ginger is extremely valuable in dyspepsia, flatulence, colic, vomiting, spas and other painful affections of the stomach, and the bowels unattended by fevers for cold, cough, asthma, dyspepsia, and indigestion. A paste of ginger is a local stimulant and rubefacient in headche, toothache, and near sightedness due to deficient contractile power of the iris; ginger powder rubbed on the extremities of the limbs checks cold perspiration and improves blood circulation in the collapse stage of cholera. Dry ginger is best given either in powder in doses of 1 to 2 gr, which may be taken with 0.5 gr of sodium carbonate or potash in gout and chronic rheumatism, or in the form of infusion in doses of 28 to 56 ml every hour for indigenous and want of appetite.

*Piper longum* Family: Piperaceae

A slender aromatic climber with perennial woody roots occurring in the hotter parts of India, from Central Himalayas to Assam, Khasi and Mikir hills, lower hills of Bengal and evergreen forests of western ghats from Konkan to Travancore; it has been recorded also from Car Nicobar Islands; Stems creeping, Jointed: young shoots downy; leaves 5-9 cm. long, 3-5 cm wide, ovate, cordate with broad rounded lobes at base, subacute, entire, glabrous; spikes cylindrical pedunculate, male larger and slender, female 1.3-2.5 cm long and 4-5 mm. diam; fruits ovoid, yellowish orange, sunk in fleshy spike.

Chemical constituents: The fruits gave positive tests for the presence of volatile oil, starch, protein and alkaloids, saponins, carbohydrates, and amygadalin, but no tannins (Dasgupta and Datta, 1980). The alkaloids isolated from roots and stems were identified as piperine and piperlongumine and also methyl 1-3,4,5-trimethoxycinnamate (Chatterjee and Datta, 1963).

Pharmacological action: Infusion is stimulant, carminative, alterative, and tonic; more powerful than black peeper; also aphrodisiac, diuretic, vermifuge, and emmenagogue. Root is stimulant. *P. longum* is reported to exhibit significant antitubercular activity (Gupta et al., 1980). The essential oil of fruit showed antibacterial, antifungal and anthelmintic activity (Bhargav and Chauhan, 1968), as well as insecticidal and insect-repellant activity. Sharma and Singh (1980) observed a marked anti-inflammatory activity of fruit decoction against carrageenin-induced rat paw edema. Kholkute et al (1979) observed that benzene extract of *P. longum* in combination with methanol extract of *Embelia ribes*berries led to inhibition of pregnancy in 80% of the animals.

Medicinal Properties and uses: The berries are a cardiac stimulant, carminative, alternative, tonic, laxative, digestive, stomachic, and antiseptic. It is given with honey in doses of 5-10 g for indigestion. Dyspepsia, flatulent colic, cough, chronic bronchitis, chest affections, and in asthma. It is also very useful in enlarged spleen, palsy, gout, rheumatism, and lumbago. Fruit is vermifuge and also used after childbirth to check post-partum hemorrhage. Root is used as stimulant. The drug is also used in snakebite and scorpion sting (Mitra and Prasad, 1941).

*Piper nigrum* Family: Piperaceae

A branching, climbing, perennial shrub, mostly round cultivated in the hot moist parts of India, Ceylon and other tropical countries; Branches stout, trailing and rooting at the nodes; leaves entire, 12.5-17.5 by 5.0-12.5 cm. very varible in breadth, some times glaucous beneath, base acute rounded or cordate, equal or unequal; flowers minute in spikes, usually dioecious, but often the female bears 2 anthers, and the male pistillode; fruiting very variable in length and robustness, rachis glabrous, fruits ovoid or globose bright nad when ripe seeds usually globose, testa thin, albumin hard.

Chemical constituents: The black pepper contains an alkaloid piperine (5 to 9%), piperdine (5%), a balsamic volatile essential oil (1 to 2%), fat (7%); mesocarp contains chavicine, a balsamic volatile oil, starch, lignin, gum, fat (1%); proteids (7%) and ash containing organic matter (5%). Chavacine is a soluble pungent concrete resin. The fruits yielded N-isobutyl eicosa-trans-2-trans-4-dienamide in addition to earlier reported piperine, piperetine, piperidine amides, viz., piperlin, piperolein A, and piperolein B (Raina et al., 1976).

Pharmacological action: *P. nigrum* is acrid, pungent hot, carminative, also used as antiperiodic. Externally, it is rubefacient and stimulant to the skin and resolvent. The extract and essential oil of *P. nigrum* is reported to the antibacterial and antifungal. The fruits exhibited taenicidal activity (Satyavati et al., 1987).

Medicinal properties and uses: A paste of black pepper is a rubefacient and stimulant; it is locally used for boils, relaxed sore throat, piles, paralytic affections, rheumatic pain, headache, prolapsed rectum, and toothache. Black pepper is aromatic, given in dyspepsia, flatulence, debility, diarrhea, cholera, disorders of the urinary system, cough, gonorrhea, and malarial fever (Nadkarni, 1954).

*Trachyspermum ammi* (*Carum copticum*) Family: Apiaceae

An erect, glabrous or minutely pubescent, branched annual, up to 90 cm. tall, cultivated almost throughout India; Stems striate; leaves rather distant, 2-3-pinnately divided, segments linear, ultimate segments 1.0-2.5 cm. long; flowers in terminal or seemingly-lateral pedunculate, compound umbels, white small; fruits ovoid, muricate, aromatic cremocarps, 2-3 mm. Long, grayish brown, mericarps compressed with distinct ridges and tubercular surface, 1-seeded.

Chemical constituents: It yields aromatic volatile oil and a crystalline substanc-steroptin-which collects on the surface of distilled water; also cumene and a terpene, "thymene". The steroptin known as crude thymol is identical with English thymol. The seeds of *Carum copticum* contain the antiseptic thymol and they yield 2 to 3% of an essential oil, which is official as oil of ajowan and contains not less than 40 to 50% of thymol $C_{10}H_4O$.

Pharmacological action: Seeds are stimulant, carminative, tonic, aromatic, antispasmodic, and antiseptic (Kapoor, 2001).

Medicinal properties and uses: Seeds are useful in flatulence, indigestion, colic, atonic dyspepsia, diarrhoea, cholera, and spasmodic affections of the bowels. Oil is also used in flatulent colic, atonic dyspepsia or diarrhea, hysteria, and indigestion. The chief importance of ajwain seeds is for production of thymol used in a number of medicinal preparations. Leaves of tender plant are used as vermicide; its juice is given for worms (Nadkarni 1954).

*Hemidesmus indicus* R. Br. Family: Asclepiadaceae

A slender, twining or prostate perennial shrub with cylindrical sterns, thickened at the nodes and aromatic roots. Leaves simple, opposite or whorled, short petioled, variable in shape from broadly ovate to oblong-elliptic, linear or linear-lanceolate, 3-10 cm long 0.3-3.8 cm wide, base acute, rounded or truncate, apex rounded or emarginated and apiculate, leathery, dark green, petioles 0.1-0.6 cm long. Flowers are small, greenish-yellow outside and purplish inside, 0.6-0.8 cm in diameter when expanded, lobes thick, ovate-oblong.

Medicinal properties and uses: The dried root and root bark are considered tonic, alternative, demulscent, diaphoretic, diuretic and blood purifying. They are used in several well-known Ayurvedic preparations for treating bowel complaints, elephantiasis, fever, hemiplegia, nausea, syphilis and vomiting. Administered in powdered from or as an infusion, decoction or syrup. The root paste is applied to the fore head to reduce fever among the Paharia in southern Bihar. A hot infusion of the root bark with milk and sugar is given to children to relieve chronic cough and diarrhoea.

*Ocimum gratissimum* Linn Family: Labiatae/Lamiaceae

A tall, much branched perennial shrub, generally 1.2-1.8 m tall, more strongly scented than other species of the genus; stem and branches sub quadrangular, woody below. Leaves 6.3-12.5 cm long and 3.8-5.7 cm wide, elliptic-lanceolate, apex acute, base cuneate, margins coarsely crenate-serrate, petioles 2.5-6.3 cm long. Flowers pale greenish-yellow, borne in simple or branched racemes, moderately closely whorled; bracts sessile, longer than the calyx 3 mm long in flower and to 6 mm long in fruit.

Medicinal properties and uses: The plant is considered digestive, tonic, stimulant, demulcent, diuretic, anti emetic, anti septic and styptic. In Ayurveda the plant is used to treat skin diseases, erysipelas, inflammations and strangury. In Unani practice, the plant in considered carminative and aphrodisiac and used to treat diseases of the brain, heart, liver and spleen, to relieve griping and piles. In Siddha, the whole plant is used as a carminative and diuretic. A decoction of the leaves is considered a useful remedy for gonorrhoea and for seminal weakness. The leaf juice is sometimes given to relieve stomachache. The oil is also used to relieve earache, toothache and abdominal colic in children.

*Sesbania grandiflora* Family: Fabaceae

A short-lived, quick-growing; soft-wooded tree, 6-9 m. high and 0.6 m. in girth. It is a native of Malaysia and is grown in many parts of India such as Punjab, Delhi, Bengal, Assam and the Andmans; Leaves 15-30 cm. long, abruptly pinnace, leaflets 41-61, linear-oblong, glabrous, 2.5-5.0 cm×0.5-1.6 cm.; racemes 2-4-flowered, short, axillary; flowers 6.0-10 cm, long with showy, fleshy white, pink, or crimson petals; pods pendulous 30.0-45.0 cm.×0.6-0.8 cm., rather flat and somewhat 4-cornered non-torulose, septate with swollen margins and 15-50 pale coloured seeds.

*Ocimum sanctum* Family: Lamiaceae

Erect, herbaceous, much-branched, softly hairy annual, 30-75 cm. high, found throughout India ascending up to 800 m in the Himalayas, and in Andaman and Nicobar islands. Leaves elliptic oblong, acute or obtuse, entire or serrate, pubescent ob both sides minutely gland-dotted; flowers purplish or crimson, in racemes, close whorled, nitlets sub-globose or broadly ellipsoid, slightly compressed, nearly smooth, pale brown or reddish, with small black markings.

Chemical constituents: The leaf contains the highest percentage of essential oil, followed by inflorescence and stem, but roots are devoid of any oil (Dey and Choudhury, 1984). Seeds contain a large amount of mucilage. Lal et al. (1979) reported the presence of 70% eugenol as a major constituent in the essential oil. The other components identified were nerol, eugenol methyl ether, caryophyllene, terpinene-4-ol, decyladehyde, γ-selinene, α-pinene, β-pinene, camphor, and carvacrol. The leaves also yield ursolic acid, apigenin, luteolin, apigenin 7-o-glucuronide, luteolin, orientin, and molludistin. Old leaves of *O. sanctum* contained 3.15% calcium, 0.34% phosphorus, and 4.97% insoluble oxalate (Singh et al., 1969).

Pharmacological action: Demulcent, expectorant, and antiperiodic. Root is fibrifuge; seeds are mucilaginous and demulcent. Dried plant is stomachic and expectorant. Leaves are anticatarrhal, expectorant, fragrant, and aromatic. *O. sanctum* leaves are reported to show abortifacient and antifertility activity (Vohra et al., 1969). Ethanolic extract (50%) of leaves shoed a hypoglycemic effect in rats and antispasmodic activity against spasmogen-induced spasms in isolated guinea pig ileum. Singh et al. (1970) reported that crude watery extract of leaves showed a transient hypotensive effect in anesthetized dogs and cats and a negative intropic and chronotropic effect on rabbit's heart. The extract inhibits spasm of smooth muscles induced by acetylcholine, carbachol, and histamine and potentiated hexobarbitone-induced hyposis in mice.

Medicinal properties and uses: Infusion of the leaves is given in malaria and as a stomachic in gastric disease of children and hepatic affections. Juice of the leaves should be taken internally and is very effective in skin disease such as itches, ringworm, and leprosy, and in impurities of the blood. Dried plant in decoction is a domestic remedy for catarrh, bronchitis, and diarrhea. Fresh leaves also cure chronic fever, hemorrhage, dysentery, and dyspepsia. With honey and ginger juice, it is a good expectorant, useful in cough, bronchitis, and children's fever. Popular as herbal tea (Nadkarni. 1954).

*Elletaria cardamomum* Family: Zingiberaceae

A tall, herbaceous perennial, with branching subterranean rootstock, from which arise a number of upright leafy shoots, 5-18 ft. high, bearing alternate, elliptical or lanceolate sheathing leaves 1-3 ft. long. Flowers borne in panicles 2.4 ft. long, arising from the base of vegetative shoots; panicles upright throughout their length or upright at first and ultimately pendent or prostrate; flowers about 1.5 in. long, white or pale green in colour with a central lip streaked with violet, borne in a close series on the rachis; they are bisexual, but self-sterile, and open in succession from the base towards the tip; Fruits trilocular capsules, fusiform to ovoid, pale green to yellow in colour, containing 15-20 hard, brownish black, angled and rugose seeds, covered by a thin mucilaginous membrane.

Chemical constituents: Seeds contain essential oil to extent of 4 to 8%. Principal constituents of oil are cineol, terpineol, terpinene, limonene, sabinene, and terpineol in form of formic and acetic acids. Aqueous portion of steam distillate of cardamom contains 0.5% of essential oil with following constants: sp gr 0.0920, nD25 1.4606; and [a]D25, O; cineol content, 80%. Borneol was identified in oil from aqueous distillate of Malabar cardamom oil. Analysis of cardamom capsule gave the following results: moisture (20.0%), protein (10.2%), ether extract (2.2%), mineral matter (5.4%), crude fiber (20.1%), carbohydrate (42.1%), calcium (0.13%), phosphorus (0.16%), and iron (5.0 mg/100 g) (Anon, 1951).

Pharmacological action: The seeds are aromatic, pungent, cardiac, tonic, stomachic, lexative, diuretic, and carminative (Kapoor 2001).

Medicinal properties and uses: The seeds are very useful in asthma, bronchitis, piles, strangury, and diseases of the bladder. As diuretic the seeds are given with honey as a corrective; the seeds are administrated in flatulence and in griping of purgative. A decoction of cardamom together with its pericarp and jaggary added is a popular home remedy to relieve giddiness caused by biliousness. A compound powder containing rqual parts of cardmom seeds, ginger, cloves, and caraway is a good stomachic in 1.5-gr doses in atonic dyspepsia. It is also very useful to check vomiting.

*Syzygium aromaticum* Family: Myrtaceae

A pyramidal or conical evergreen tree 9-12 m. high sometimes taller; Main stems erect, c. 100 cm. in girth, often forking at a height of 1.5-1.8 m.; bark smooth, grey; leaves lanceolate, in pairs, acute at both ends, 7.5-12.3 cm.×2.5-3.75 cm., gland-dotted, fragrant; flower-buds borne in small clusters at the ends of branches, greenish, turning pink at the time of maturity, aromatic; drupes (MOTHER-OF-CLOVE), fleshy, dark pink, 2.5 cm. long×1.5 cm. thick; seeds oblong, soft, grooved on one side, 1.5 cm. long.

*Catharanthus roseus* Family: Apocynaceae

An erect, much branched, annual or perennial herb 30-90 cm in height, probably native to Malagasy, occasionally found wild but mostly naturalized up to an altitude of 1,300 m, and commonly grown in gardens throughout the country. Leaves oblong-elliptic, acute, rounded apex glossy, slightly foetid; flowers fragrant, white to pinkish purple in terminal or axillary cymose clusters; follicle hairy, many seeded, 2-3 cm long; seeds oblong, minute, black.

*Cuminum cyminum* Family: Apiaceae

A small, slender annual herb about 1 ft. high, with a much-branched angular or striated stem bearing 2 or 3 partite linear leaves; leaves bluish green in colour and having sheathing bases. The flowers are white or rose coloured borne in compound umbels; fruits are grayish, about ¼ in. long, tapering towards both base and apex and compressed laterally with ridges covered by papillose hairs. The hairs may be absent in some forms.

Chemical constituents: Analysis of seeds gave the following results: moisture (11.9%), protein (18.7%), ether extract (15.0%), carbohydrates (36.6%), fiber 912.05), mineral matter (5.8%), calcium (1.08%), phosphorus (0.49%), iron (31.0 mg/100 g), carotene calculated as vitamin A (870 IU/100 g), and vitamin C 3 mg/100 g) (Anon, 1941).

Pharmacological action: Seeds are carminative, aromatic, stomachic, stimulant, and astringent (Kapoor 2001).

Medicinal properties and uses: Seeds have cooling effect and therefore form an ingredient of most prescriptions for gonorrhea, chronic diarrhea, and dyspepsia. It is also useful in hoarseness of voice, dyspepsia, and chronic diarrhea in a dose of 1 to 2 gr. Cumin oil can be readily converted artificially in to thymol; thymol is used as an anthelmintic against hook worm infections and is also an antiseptic, forming part of many proprietary preparations.

*Nigella sativum* Linn. Family: Ranunculaceae

Small herb, c. 45 cm. high, native of Levant, said to be cultivated or occasionally found as a weed in Punjab, Himachal Pradesh, Bihar and Assam. Leaves 2-3 pinnatisect, 2.5-5.0 cm. long, cut into linear-lanceolate segments; flowers pale blue, 2.0-2.5 cm. across, without involucre, on solitary long peduncles; seeds trigonous, black, rugulose-tubercular.

Chemical constituents: Analysis of black cumin gave the following values: total ash, 3.8-5.3: ash insol. In HCL, 0.0-0.05; volatile oil, 0.5-1.6; either extr, (fatty oil), 35.6-41.6; and alcoholic acidity (as oleic acid), 3.4-6.3%. The seeds give on steam-distillation a yellowish brown volatile oil with an unpleasant odour. It has the following characteristics: $d^{15}$, 0.875-0.886; 1.4836-1.4844; $[a]_D$, +1.43° to +2.86°; acid val., up to 1.9; ester val., 1-31.6; ester val. after acetylation, 15-73; solution in 2-4.5 or more volumes of 90% alcohol. The oil contains carvone (45-60%), d-limonene and cymene. A carbonyl compound, nigellone ($C_{18}H_{22}O_4$, m.p. 195-97°), which protects guinea pigs against histamine induced bronchospasm has been isolated from the oil. Preliminary clinical trials indicate its possible therapeutic use in some conditions of cough and bronchial asthma.

The fatty oil obtained by the expression of seeds is reported to be useful for edible purposes. The fatty acids of the oil are as follows: myristic, 0.26; palmatic, 6.31; stearic, 2.45; oleic, 44.45; and linoleic, 35.99%, the component glycerides of the oil are the following: trilinolein, 2: oleodilinolein, 25; dioleolinolein, 43; palmito-oleolinolein (containing small amount of myristic acid.), 24; and stearo-oleolinolein, 7%; glycerides of some volatile acids are also present in the oil in small quantities.

The present invention provides a novel nicotine free anti-cigarette herbal formulation as an antidote to the poisoning effects of tobacco products such as Cigarettes, Gutka, Pan masala and other similar tobacco related products. Novelty of the invention lies in the herbal formulation, its nicotine free nature and its ability to prevent damage caused due to smoking.

The formulation of the invention comprises essentially an effective amount of sterilized dried plant powder/extracts obtained from *Sesbania grandiflora, Catharanthus roseus, Ocimum sanctum, Myristica fragrans, Elettaria cardamomum, Carum copticum, Syzygium aromaticum, Cinnamomum tamala, Acorus calamus, Zingiber officinale, Piper nigrum, Cinnamomum zeylanicum, Cuminum cyminum, Nigella sativum, Cinnamomum camphora, Piper longum Ocimum gratssimum, Hemidesmus indicus* and optionally with pharmaceutical additives. The extracts are comprise powdered plant parts or lyophilized extracts of plants *Sesbania grandiflora, Ocimum sanctum, Myristica fragrans, Elettaria cardamomum, Carum copticum, Syzygium aromaticum, Cinnamomum tamala, Acorus calamus, Zingiber officinale, Piper nigrum, Cinnamomum zeylanicum, Cuminum cyminum, Nigella sativum, Cinnamomum camphora, Piper longum, Ocimum gratssimum, Hemidesmus indicus* and *Catharanthus roseus*. The extracts of the plants are mixed in the ratio *Sesbania grandiflora* (15-20%), *Hemidesmus indicus* (1-2%), *Ocimum sanctum* (2-4%), *Myristica fragrans* (2-3)%, *Elettaria cardamomum* (1-2%), *Carum copticum* (0.5-1%), *Syzygium aromaticum* (1-2%), *Cinnamomum tamala* (1-2%), *Acorus calamus* (0.5-1%), *Zingiber officinale* (1-2%), *Piper nigrum* (1-2%), *Cinnamomum zeylanicum* (1-2%), *Cuminum cyminum* (1-2%), *Nigella sativum* (1-2%), *Cinnamomum camphora* (0.2-0.5%), *Piper longum* (1-2%), *Ocimum gratissimum* (1-2%) and *Catharanthus roseus* (10-15%) along with conventional additives to form an oral dosage form.

The composition of the invention is nicotine free and acts as an antidote to the poisoning effects of tobacco and tobacco related products. The composition is effective in controlling a number of complications associated with cigarette smoking. It is also non-toxic and safe to use. Moreover the composition reduces tobacco-induced toxicity. The composition has the potential to maintain the homeostasis in general and has the potential to provide a supportive and protective cover to the cellular and organic functions of the heart, the lungs, the blood vessels, and the gastro-intestinal epithelium and mucosa in particular.

The composition can be used as an oral dosage form such as syrup, tablet, capsule and a powder/spray. The extracts are alcoholic extracts wherein the alcohol is preferably ethanol. The extracts of plants are 50% aqueous alcoholic extract. The composition itself comprises about 15-50% wt. of the total formulation. The plant powder/extract of *Sesbania grandiflora* is obtained from seeds or leaves, the plant powder/extract of *Catharanthus roseus* is obtained from leaves, the plant powder/extract of *Hemidesmus indicus* is obtained from stem, the plant powder/extract of *Ocimum sanctum* is obtained from leaves, the plant powder/extract of *Myristca fragrans* is obtained from fruits, the plant powder/extract of *Elettaria cardamomum* is obtained from fruits, the plant powder/extract of *Carum copticum* is obtained from fruits, the plant powder/extract of *Syzygium aromaticum* is obtained from flowers, the plant powder/extract of *Cinnamomum tamala* is obtained from leaves, the plant powder/extract of *Acorus calamus* is obtained from rhizomes, the plant powder/extract of *Zingiber officinale* is obtained from rhizome, the plant powder/extract of *Piper nigrum* is obtained from fruits, the plant powder/extract of *Cinnamomum zeylanicum* is obtained from bark, the plant powder/extract of *Cuminum cyminum* is obtained from fruit, the plant powder/extract of *Carum carvi* is obtained from fruit, the plant powder/extract of *Cinnamomum camphora* is obtained from bark or leaves, and the plant powder/extract of *Piper longum* is obtained from fruit or roots. The composition can be mixed with conventional additives such as binders which are preferably selected from starch, starch paste, gum acacia and carboxy methyl cellulose. Talc (Purified), Magnesium Stearate, Sodium Methyl Paraben and Sodium Propyl Paraben. Diluents can also be used such as lactose. Lactose and starch can also be used as lubricants. The composition is preferably used with a vehicle comprising 66.7% w/w sugar syrup.

The composition of the invention is prepared by:
(a) obtaining the part of medicinal plants from a group comprising leaves, root and aerial parts, rhizomes,
(b) drying the plant material in shade,
(c) powdering the dried plant material to a coarse powder.
(d) sterilizing the plant powder
(e) using the powder as such or extracting the powdered dried plant material with (40-50% aqueous ethanol) at 25-35° C.

(f) extracting the plant material with aqueous alcohol in the ratio of 1:8 to 1:15 for 4-7 days (g) concentrating the obtained extract at under reduced pressure at 40-60° C.

(h) lyophilising the concentrated extract for complete removal of solvent.

It was observed that the formulation at a dose of more than 1000 mg/kg did not cause any biochemical changes in serum or any significant change in the organ weight or any change in hematological parameters. It was further observed that the formulation at a dose of 100-200-mg/kg showed stoppage of smoking in 3-10 weeks treatment as well as showed free radical scavenging property and potent antioxidant activity.

It is therefore noted that the formulation is useful as an antidote to the effects of tobacco as well as helps prevent smoking.

The invention is further illustrated by the following non-limiting examples:

Formulation (F1)

| | |
|---|---|
| Sesbania grandiflora | (18%) |
| Ocimum sanctum | (3%) |
| Myristica fragrans | (2%) |
| Elettaria cardamomum | (1%) |
| Carum copticum | (1%) |
| Syzygium aromaticum | (2%) |
| Cinnamomum tamala | (2%) |
| Acorus calamus | (0.5%) |
| Zingiber officinale | (1.5%) |
| Piper nigrum | (1%) |
| Cinnamomum zeylanicum | (2%) |
| Cuminum cyminum | (2%) |
| Nigella sativum | (2%) |
| Cinnamomum camphora | (0.5%) |
| Piper longum | (2%) |
| Catharanthus roseus | (14%) |
| Starch | (2%) |
| Lactose | (QS to make 100%) |

The first step in preparation of these formulations involves a process for making the plant material suitable for formulating into a tablet, capsule or liquid dosage form. The specified portion of plant is collected and dried under shade at room temperature (25-35° C.) for 72 hours or till the material dries. The material is then powdered into a fine powder. The dried material (1 Kg) is then powdered and used as such or extracted with 50% aqueous alcohol (3 L) for 5 days. Thereafter, the solvent was decanted and filtered if necessary to remove the plant debris.

The extract is then concentrated under vacuum at less than 50° C. the extract is then lyophilised to obtain the extract in powder form. 15 g of starch is mixed with water and heated to form a paste. The weighed quantities of the plant extracts are then blended with starch paste and then lactose is added quantity sufficient to make 100 g. The ingredients are then mixed properly with the starch paste to form a mass. The mass is then granulated in a granulator and then dried at 104° F. and screen through 16-mesh screen. Talc is added to the dried granules and they are then punched in a tablet-punching machine to form uniform tablets. Extracts were added in proper ratio to prepare syrup. Syrup was prepared according to Indian Pharmacopoeia 1966.

Formulation (F2)

(The critical components in this formulation F2 are Sesbania grandiflora and Ocimum gratissimum)

| | |
|---|---|
| Sesbania grandiflora | (20%) |
| Hemidesmus indicus | (2%) |
| Ocimum sanctum | (3%) |
| Myristica fragrans | (3%) |
| Elettaria cardamomum | (1%) |
| Carum copticum | (0.5%) |
| Syzygium aromaticum | (2%) |
| Cinnamomum tamala | (2%) |
| Acorus calamus | (0.5%) |
| Zingiber officinale | (2%) |
| Piper nigrum | (1%) |
| Cinnamomum zeylanicum | (2%) |
| Cuminum cyminum | (2%) |
| Nigella sativum | (1%) |
| Cinnamomum camphora | (0.2%) |
| Piper longum | (2%) |
| Ocimum gratissimum | (2%) |
| Catharanthus roseus | (15%) |
| Starch | (2%) |
| Lactose | (QS to make 100%) |

The first step in the preparation of these formulations involves a process for making the plant material suitable for formulating into a tablet, capsule or liquid dosage form. Specified portion of plant is collected and dried under shade at room temperature (25-35° C.) for 72 hours or till the material dries. The material is then powdered into a fine powder. Dried material (1 Kg) is then powdered and used as such or extracted with 50% aqueous alcohol (3 L) for 5 days. The solvent is then decanted and filtered if necessary to remove plant debris.

The extract is then concentrated under vacuum at less than 50° C. Then the extract is lyophilised to obtain the extract in powder form 0.15 g of starch is mixed with water and heated to form a paste. The weighed quantities of the plant extracts are then blended with starch paste and lactose is then added in a quantity sufficient to make 100 g. The ingredients are then mixed properly with starch paste to form a mass. The mass is then granulated in a granulator and then dried 104° F. and screen through 16-mesh screen. Talc is added to the dried granules and then they are punched in the tablet-punching machine to form uniform tablets. Extracts were added in proper ratio to prepare syrup. The syrup was prepared according to Indian Pharmacopoeia 1966.

TABLE 1

Effect of anticigarette herbal formulation on antioxidant enzymes

| Groups | GSH (µg/mg protein) | SOD (µg/mg protein) | Catalase (µg/mg protein) | TBARS (nmoles/mg protein) |
|---|---|---|---|---|
| Control | 3.50 ± 0.28 | 1.24 ± 0.29 | 25.2 ± 1.8 | 1.46 ± 0.07 |
| F1 (100 mg/kg) | 3.67 ± 0.23 | 1.27 ± 0.30 | 28.2 ± 2.1 | 1.41 ± 0.06 |
| F1 (200 mg/kg) | 3.81 ± 0.18 | 1.30 ± 0.32 | 31.7 ± 2.4 | 1.38 ± 0.05 |
| F2 (100 mg/kg) | 4.51 ± 0.16$^b$ | 1.58 ± 0.07$^b$ | 47.99 ± 3.45$^a$ | 1.01 ± 0.08$^b$ |
| F2 (200 mg/kg) | 5.75 ± 0.09$^d$ | 1.98 ± 0.12$^c$ | 79.29 ± 2.76$^c$ | 0.79 ± 0.04$^d$ |

The values represent the means ± S. E. M; n = 6.
P: $^a$<0.5, $^b$<0.05, $^c$<0.01 and $^d$<0.001 compared to respective control group Formulation F1 contains *Sesbania grandiflora* (15-20%), *Ocimum sanctum* (2-4%), *Myristica fragrans* (2-3)%, *Elettaria cardamomum* (1-2%), *Carum copticum* (0.5-1%), *Syzygium aromaticum* (1-2%), *Cinnamomum tamala* (1-2%), *Acorus calamus* (0.5-1%), *Zingiber officinale* (1-2%), *Piper nigrum* (1-2%), *Cinnamomum zeylanicum* (1-2%), *Cuminum* cyminum (1-2%), *Nigella sativum* (1-2%), *Cinnamomum camphora* (0.2-0.5%), *Piper longum* (1-2%), and *Catharanthus roseus* (10-15%).

Formulation F2 contains *Sesbania grandiflora* (15-20%), *Hemidesmus indicus* (1-2%), *Ocimum sanctum* (2-4%), *Myristica fragrans* (2-3)%, *Elettaria cardamomum* (1-2%), *Carum copticum* (0.5-1%), *Syzygium aromaticum* (1-2%), *Cinnamomum tamala* (1-2%), *Acorus calamus* (0.5-1%), *Zingiber officinale* (1-2%), *Piper nigrum* (1-2%), *Cinnamomum zeylanicum* (1-2%), *Cuminum cyminum* (1-2%), *Nigella sativum* (1-2%), *Cinnamomum camphora* (0.2-0.5%), *Piper longum* (1-2%), *Ocimum gratissimum* (1-2%) and *Catharanthus roseus* (10-15%).

The results in Table 1 indicate that there is a significant increase in glutathione peroxidase (GSH), Superoxide dismutase (SOD) and Catalase (CAT) in formulation F2 than that of F1. It indicates that the enzymatic antioxidants (GSH, SOD and CAT); Thiobarbituric acid reactive substances (TBARS) were decreased there radicals are scavenged by the formulation F2. Therefore the body defensive system was increased.

TABLE 2

Toxicity Profile on haematological changes of formulation F2.

| | Periods | | |
|---|---|---|---|
| | 0 Day | 30$^{th}$ Day | 60$^{th}$ Day |
| B. Weight (Kg) | 48 kg | 48.5 kg | 52.5 kg |
| B.P. (mm Hg) | 122/80 | 120/80 | 124/80 |
| T.C. (ces/cmm) | 10100 | 9700 | 9100 |
| D.C. (%) | P51; N46, B1; E2 | P50; N47; B NIL; E3 | P48; N46; B1; E5 |
| H.b. (gm %) | 10.8 gm % | 11.6 gm % | 12.1 gm % |
| ESR (mm/h) | 55 mm/h | 45 mm/h | 32 mm/h |
| RBS (mg %) | 89 mg % | 105 mg % | 102 mg % |
| Choles. (T)(mg) | 161 mg | 167 mg | 166 mg |
| SGOT (IU/L) | 24.2 IU/L | Not studied | 24.2 IU/L |
| SGPT (IU/L) | 22 IU/L | Not studied | 22 IU/L |
| S. Biliru (T) (mg/dl) | 0.9 mg/dl | Not studied | 0.8 mg/dl |
| A. Phos (KA/Units) | 7.2 ka/units | Not studied | 7.1 ka/units |
| Protein (T) (gr/dl) | 6.3 gr/dl | Not studied | 6.5 gr/dl |
| B. Urea (mg/dl) | 23 mg/dl | Not studied | 24 mg/dl |
| S. Creat (mg/dl) | 1.00 mg/dl | Not studied | 1.00 mg/dl |
| Uric acid (mg/dl) | 3.5 mg/dl | Not studied | 3.6 mg/dl |

Formulation F2 contains *Sesbania grandiflora* (15-20%), *Hemidesmus indicus* (1-2%), *Ocimum sanctum* (2-4%), *Myristica fragrans* (2-3)%, *Elettaria cardamomum* (1-2%), *Carum copticum* (0.5-1%), *Syzygium aromaticum* (1-2%), *Cinnamomum tamala* (1-2%), *Acorus calamus* (0.5-1%), *Zingiber officinale* (1-2%), *Piper nigrum* (1-2%), *Cinnamomum zeylanicum* (1-2%), *Cuminum cyminum* (1-2%), *Nigella sativum* (1-2%), *Cinnamomum camphora* (0.2-0.5%), *Piper longum* (1-2%), *Ocimum gratissimum* (1-2%) and *Catharanthus roseus* (10-15%).

The results in Table 2 indicate that there is no change in the hematological parameters with active formulation F2.

TABLE 3

Clinical trials: Weekly analysis of subjects regarding smoking of effective formulation F2

| Groups | | 1$^{st}$ Week | 2$^{nd}$ Week | 3$^{rd}$ Week | 4$^{th}$ Week | 5$^{th}$ Week | 6$^{th}$ Week | 7$^{th}$ Week | 8$^{th}$ Week |
|---|---|---|---|---|---|---|---|---|---|
| Group I | Stopped | 0 | 1 | 10 | 13 | 15 | 16 | 17 | 17 |
| | Reduced | 3 | 9 | 5 | 3 | 3 | 2 | 1 | 1 |
| | No Result | 16 | 9 | 4 | 3 | 1 | 1 | 1 | 1 |
| Group II | Stopped | 0 | 0 | 4 | 16 | 22 | 27 | 35 | 41 |
| | Reduced | 38 | 39 | 36 | 29 | 25 | 22 | 17 | 11 |
| | No Result | 18 | 17 | 16 | 11 | 9 | 7 | 4 | 4 |
| Group III | Stopped | 0 | 0 | 3 | 5 | 9 | 13 | 14 | 14 |
| | Reduced | 3 | 7 | 11 | 12 | 8 | 4 | 3 | 3 |
| | No Result | 22 | 18 | 11 | 8 | 8 | 8 | 8 | 8 |

Formulation F2 contains *Sesbania grandiflora* (15-20%), *Hemidesmus indicus* (1-2%), *Ocimum sanctum* (2-4%), *Myristica fragrans* (2-3)%, *Elettaria cardamomum* (1-2%), *Carum copticum* (0.5-1%), *Syzygium aromaticum* (1-2%), *Cinnamomum tamala* (1-2%), *Acorus calamus* (0.5-1%), *Zingiber officinale* (1-2%), *Piper nigrum* (1-2%), *Cinnamomum zeylanicum* (1-2%), *Cuminum cyminum* (1-2%), *Nigella sativum* (1-2%), *Cinnamomum camphora* (0.2-0.5%), *Piper longum* (1-2%), *Ocimum gratissimum* (1-2%) and *Catharanthus roseus* (10-15%).

Group I contains 19 volunteers habituated to smoking: On 8$^{th}$ week 17 volunteers stopped smoking out of 19 volunteers.

Group II contains 56 volunteers habituated to smoking: On 8$^{th}$ week 41 volunteers stopped smoking out of 56 volunteers.

Group III contains 25 volunteers habituated to smoking: On 8$^{th}$ week 14 volunteers stopped smoking out of 25 volunteers.

TABLE 4

Effect of anticigarette herbal formulation F2 on productive cough (FIG. 1)

| Group I | | Group II | | Group III | |
|---|---|---|---|---|---|
| Before Treatment | After Treatment | Before Treatment | After Treatment | Before Treatment | After Treatment |
| 14 | 3 | 46 | 11 | 22 | 6 |

Formulation F2 contains *Ocimum sanctum* (2-4%), *Myristica fragrans* (2-3)%, *Elettaria cardamomum* (1-2%), *Carum copticum* (0.5-1%), *Syzygium aromaticum* (1-2%), *Cinnamomum tamala* (1-2%), *Acorus calamus* (0.5-1%), *Zingiber officinale* (1-2%), *Piper nigrum* (1-2%), *Cinnamomum zeylanicum* (1-2%), *Cuminum cyminum* (1-2%), *Nigella sativum* (1-2%), *Cinnamomum camphora* (0.2-0.5%), *Piper longum* (1-2%), *Ocimum gratissimum* (1-2%) and *Catharanthus roseus* (10-15%).

Group I: Randomly selected smokers having productive cough (14 volunteers) after exposure to the formulation F2 only 3 smokers showed suffering from dry cough and the percent protection is 78.6%.

Group II: Randomly selected smokers having productive cough (46 volunteers) after exposure to the formulation F2 only 11 smokers showed suffering from dry cough and the percent protection is 76.08%.

Group III: Randomly selected smokers having productive cough (22 volunteers) after exposure to the formulation F2 only 11 smokers showed suffering from dry cough and the percent protection is 72.7%.

*Carum copticum* (0.5-1%), *Syzygium aromaticum* (1-2%), *Cinnamomum tamala* (1-2%), *Acorus calamus* (0.5-1%), *Zingiber officinale* (1-2%), *Piper nigrum* (1-2%), *Cinnamomum zeylanicum* (1-2%), *Cuminum cyminum* (1-2%), *Nigella sativum* (1-2%), *Cinnamomum camphora* (0.2-0.5%), *Piper longum* (1-2%), *Ocimum gratissimum* (1-2%) and *Catharanthus roseus* (10-15%).

BUN: Biliruin
GOT: Aspartate amino transferase
GPT: Alanine amino transferase
ALP: Alkaline phosphatase The results in Table 5 indicate that there is no change in the biochemical parameters with the active formulation F2.

TABLE 5

Biochemical parameters: A 14-day repeated oral toxicity study of anticigarette herbal formulation F2 in rats. DOSE: 1000 mg/kg b.w

| RAT NO. | Sex | BUN (mg/dl) | GOT (IU/l) | GPT (IU/l) | ALP (IU/l) | Protein (g/dl) | Albumin (g/dl) | Creatinine (mg/dl) | Glucose (mg/dl) |
|---|---|---|---|---|---|---|---|---|---|
| 31 | M | 12.01 | 112.1 | 35.12 | 234.0 | 6.355 | 3.022 | 0.3379 | 94.52 |
| 32 | M | 10.40 | 114.3 | 41.38 | 264.3 | 6.357 | 3.318 | 0.4379 | 81.26 |
| 33 | M | 12.20 | 117.8 | 52.37 | 116.6 | 7.021 | 2.317 | 0.5200 | 92.19 |
| 34 | M | 12.41 | 108.4 | 53.26 | 231.0 | 6.203 | 2.428 | 0.5210 | 104.30 |
| 35 | M | 10.76 | 131.6 | 40.45 | 182.4 | 6.153 | 3.128 | 0.5265 | 103.90 |
| 36 | F | 13.42 | 122.1 | 34.90 | 175.5 | 6.214 | 3.319 | 0.6179 | 81.36 |
| 37 | F | 16.62 | 126.1 | 63.71 | 210.1 | 6.257 | 3.226 | 0.8110 | 82.34 |
| 38 | F | 12.79 | 107.2 | 62.53 | 225.6 | 5.826 | 3.329 | 0.6389 | 82.88 |
| 39 | F | 11.53 | 116.4 | 44.44 | 241.6 | 6.326 | 2.746 | 0.5689 | 81.03 |
| 40 | F | 10.56 | 111.6 | 67.76 | 202.2 | 6.327 | 2.943 | 0.6100 | 121.00 |

Formulation F2 contains *Sesbania grandiflora* (15-20%), *Hemidesmus indicus* (1-2%), *Ocimum sanctum* (2-4%), *Myristica fragrans* (2-3)%, *Elettaria cardamomum* (1-2%),

TABLE 6

Individual Percent Organ Weights (%) after administration of anticigarette herbal formulation F2

| GROUP/ DOSE | ANIMAL NO. | Sex | BRAIN | HEART | LIVER | SPLEEN | ADRENAL (L) | ADRENAL (R) | KIDNEY (L) | KIDNEY (R) | GONAD (L) | GONAD (R) |
|---|---|---|---|---|---|---|---|---|---|---|---|---|
| | 31 | M | 1.757 | 1.026 | 11.637 | 1.326 | 0.030 | 0.030 | 1.067 | 1.080 | 1.551 | 1.654 |
| | 32 | M | 1.789 | 0.875 | 11.705 | 1.167 | 0.033 | 0.029 | 1.131 | 1.062 | 1.626 | 1.565 |
| | 33 | M | 1.664 | 1.173 | 11.776 | 1.252 | 0.010 | 0.029 | 1.134 | 1.113 | 1.524 | 1.513 |
| | 34 | M | 1.918 | 1.001 | 11.376 | 1.155 | 0.034 | 0.034 | 1.085 | 1.066 | 1.641 | 1.654 |
| | 35 | M | 1.836 | 1.091 | 13.211 | 1.305 | 0.035 | 0.038 | 1.194 | 1.187 | 1.725 | 1.714 |
| | 36 | F | 1.889 | 1.068 | 111015 | 1.219 | 0.030 | 0.023 | 1.150 | 1.169 | 0.068 | 0.063 |
| | 37 | F | 1.478 | 0.973 | 11.238 | 1.582 | 0.032 | 0.034 | 1.117 | 1.097 | 0.054 | 0.049 |
| | 38 | F | 1.877 | 1.013 | 11.405 | 0.982 | 0.032 | 0.030 | 1.118 | 1.162 | 0.041 | 0.087 |
| | 39 | F | 1.857 | 1.062 | 11.796 | 1.472 | 0.019 | 0.020 | 1.067 | 1.093 | 0.074 | 0.071 |
| | 40 | F | 1.923 | 1.152 | 13.025 | 1.298 | 0.037 | 0.037 | 1.187 | 1.196 | 0.075 | 0.041 |

M—MALE;
F—FEMALE

Formulation F2 contains *Sesbania grandiflora* (15-20%), *Hemidesmus indicus* (1-2%), *Ocimum sanctum* (2-4%), *Myristica fragrans* (2-3)%, *Elettaria cardamomum* (1-2%), *Carum copticum* (0.5-1%), *Syzygium aromaticum* (1-2%), *Cinnamomum tamala* (1-2%), *Acorus calamus* (0.5-1%), *Zingiber officinale* (1-2%), *Piper nigrum* (1-2%), *Cinnamomum zeylanicum* (1-2%), *Cuminum cyminum* (1-2%), *Nigella sativum* (1-2%), *Cinnamomum camphora* (0.2-0.5%), *Piper longum* (1-2%), *Ocimum gratissimum* (1-2%) and *Catharanthus roseus* (10-15%).

The results in Table 6 indicate that there is no change in the organ weight parameters with the active formulation F2.

We claim:

1. A mixture of sterilized dried plant powders or aqueous alcoholic extracts of *Sesbania grandiflora, Catharanthus roseus, Ocimum sanctum, Myristica fragrans, Elettaria cardamomum, Carum copticum, Syzygium aromaticum, Cinnamomum tamala, Acorus calamus, Zingiber officinale, Piper nigrum, Cinnamomum zeylanicum, Cuminum cyminum, Nigella sativum, Cinnamomum camphora, Piper longum, Ocimum gratissimum, Hemidesmus indicus.*

2. Composition as claimed in claim 1 wherein the mixture is admixed with pharmaceutically acceptable additives.

3. Composition as claimed in claim 1 wherein the plant extracts are mixed in the following ratio: *Sesbania grandiflora* 15-20%, *Hemidesmus indicus* 1-2%, *Ocimum sanctum* 2-4%, *Myristica fragrans* 2-3%, *Elettaria cardamomum* 1-2%, *Carum copticum* 0.5-1%, *Syzygium aromaticum* 1-2%, *Cinnamomum tamala* 1-2%, *Acorus calamus* 0.5-1%, *Zingiber officinale* 1-2%, *Piper nigrum* 1-2%, *Cinnamomum zeylanicum* 1-2%, *Cuminum cyminum* 1-2%, *Nigella sativum* 1-2%, *Cinnamomum camphora* 0.2-0.5%, *Piper longum* 1-2%, *Ocimum gratissimum* 1-2% and *Catharanthus roseus* 10-15% and one or more additives to form an oral dosage form.

4. Composition as claimed in claim 1 wherein the mixture is nicotine free.

5. Composition as claimed in claim 3 wherein the oral dosage form is selected from the group consisting of syrup, tablet, capsule, powder and spray.

6. Composition as claimed in claim 1 wherein the alcohol is ethanol.

7. Composition as claimed in claim 1 wherein the plant powder/extract of *Sesbania grandiflora* is obtained from seeds or leaves.

8. Composition as claimed in claim 1 wherein the plant powder/extract of *Catharanthus roseus* is obtained from leaves.

9. Composition as claimed in claim 1 wherein the plant powder/extract of *Hemidesmus indicus* is obtained from stem.

10. Composition as claimed in claim 1 wherein the plant powder/extract of *Ocimum sanctum* is obtained from leaves.

11. Composition as claimed in claim 1 wherein the plant powder/extract of *Myristca fragrans* is obtained from fruits.

12. Composition as claimed in claim 1 wherein the plant powder/extract of *Elettaria cardamomum* is obtained from fruits.

13. Composition as claimed in claim 1 wherein the plant powder/extract of *Carum copticum* is obtained from fruits.

14. Composition as claimed in claim 1 wherein the plant powder/extract of *Syzygium aromaticum* is obtained from flowers.

15. Composition as claimed in claim 1 wherein the plant powder/extract of *Cinnamomum tamala* is obtained from leaves.

16. Composition as claimed in claim 1 wherein the plant powder/extract of *Acorus calamus* is obtained from rhizomes.

17. Composition as claimed in claim 1 wherein the plant powder/extract of *Zingiber officinale* is obtained from rhizome.

18. Composition as claimed in claim 1 wherein the plant powder/extract of *Piper nigrum* is obtained from fruits.

19. Composition as claimed in claim 1 wherein the plant powder/extract of Cinnamomum zeylanicum is obtained from bark.

20. Composition as claimed in claim 1 wherein the plant powder/extract of *Cuminum cyminum* is obtained from fruit.

21. Composition as claimed in claim 1 wherein the plant powder/extract of *Carum carvi* is obtained from fruit.

22. Composition as claimed in claim 1 wherein the plant powder/extract of *Cinnamomum camphora* is obtained from bark or leaves.

23. Composition as claimed in claim 1 wherein the plant powder/extract of *Piper longum* is obtained from fruit or roots.

24. Composition as claimed in claim 1 wherein the plant powder/extract of *Ocimum gratissimum* is obtained from leaves.

25. Composition as claimed in claim 2 wherein the additive is a binder selected from the group consisting of starch, starch paste, gum acacia, carboxy methylcellulose, Talc (Purified), Magnesium Stearate, Sodium Methyl Paraben and Sodium Propyl Paraben.

26. Composition as claimed in claim 2 wherein the additive is a diluent comprising lactose.

27. Composition as claimed in claim 2 wherein the additive used is a lubricant selected from the group consisting of starch and lactose.

28. Composition as claimed in claim 2 wherein the mixture is mixed with a vehicle comprising 66.7% w/w sugar syrup.

29. Composition as claimed in claim 1 wherein the mixture is non-toxic and safe to use.

30. A method for preparing a mixture of sterilized dried plant powders of *Sesbania grandiflora, Catharanthus roseus, Ocimum sanctum, Myristica fragrans, Elettaria cardamomum, Carum copticum, Syzygium aromaticum, Cinnamomum tamala, Acorus calamus, Zingiber officinale, Piper nigrum, Cinnamomum zeylanicum, Cuminum cyminum, Nigella sativum, Cinnamomum camphora, Piper longum, Ocimum gratissimum,* and *Hemidesmus indicus* the method comprising:
    (a) selecting plant parts from the group consisting of leaves, root, aerial parts, rhizomes and any combination thereof of said plants;
    (b) drying the selected plant parts in shade;
    (c) powdering the dried plant parts to a coarse powder;
    (d) sterilizing the plant powders.

31. A method as claimed in claim 30, further comprising:
    (e) extracting the plant powders with aqueous alcohol;
    (f) concentrating the obtained extracts;
    (g) lyophilizing the concentrated extracts for complete removal of solvent to produce the mixture of plant powders.

32. A method as claimed in claim 31 wherein the extraction in step (e) is carried out with 40-50% aqueous ethanol and at a temperature in the range of 25-35° C.

33. A method as claimed in claim 31 wherein the plant materials are extracted with aqueous alcohol in a ratio of 1:8 to 1:15 for 4-7 days.

34. A method as claimed in claim 31 wherein the obtained extracts are concentrated in step (f) under reduced pressure at 40-60° C.

35. A method as claimed in claim 30 wherein the mixture is admixed with pharmaceutically acceptable additives.

36. A method as claimed in claim 30 wherein the plant extracts are mixed in the following ratio: *Sesbania grandiflora* 15-20%, *Hemidesmus indicus* 1-2%, *Ocimum sanctum* 2-4%, *Myristica fragrans* 2-3%, *Elettaria cardamomum* 1-2%, *Carum copticum* 0.5-1%, *Syzygium aromaticum* 1-2%, *Cinnamomum tamala* 1-2%, *Acorus calamus* 0.5-1%, *Zingiber officinale* 1-2%, *Piper nigrum* 1-2%, *Cinnamomum zeylanicum* 1-2%, *Cuminum cyminum* 1-2%, *Nigella sativum* 1-2%, *Cinnamomum camphora* 0.2-0.5%, *Piper longum* 1-2%, *Ocimum gratissimum* 1-2% and *Catharanthus roseus* 10-15% and one or more additives to form an oral dosage form.

37. A method as claimed in claim 30 wherein the mixture is nicotine free.

38. A method as claimed in claim 36 wherein the oral dosage form is selected from the group consisting of syrup, tablet, capsule, powder and spray.

39. A method as claimed in claim 31 wherein the alcohol is ethanol.

40. A method as claimed in claim 30 wherein the plant powder/extract of *Sesbania grandiflora* is obtained from seeds or leaves.

41. A method as claimed in claim 30 wherein the plant powder/extract of *Catharanthus roseus* is obtained from leaves.

42. A method as claimed in claim 30 wherein the plant powder/extract of *Hemidesmus indicus* is obtained from stem.

43. A method as claimed in claim 30 wherein the plant powder/extract of *Ocimum sanctum* is obtained from leaves.

44. A method as claimed in claim 30 wherein the plant powder/extract of *Myristca fragrans* is obtained from fruits.

45. A method as claimed in claim 30 wherein the plant powder/extract of *Elettaria cardamomum* is obtained from fruits.

46. A method as claimed in claim 30 wherein the plant powder/extract of *Carum copticum* is obtained from fruits.

47. A method as claimed in claim 30 wherein the plant powder/extract of *Syzygium aromaticum* is obtained from flowers.

48. A method as claimed in claim 30 wherein the plant powder/extract of *Cinnamomum tamala* is obtained from leaves.

49. A method as claimed in claim 30 wherein the plant powder/extract of *Acorus calamus* is obtained from rhizomes.

50. A method as claimed in claim 30 wherein the plant powder/extract of *Zingiber officinale* is obtained from rhizome.

51. A method as claimed in claim 30 wherein the plant powder/extract of *Piper nigrum* is obtained from fruits.

52. A method as claimed in claim 30 wherein the plant powder/extract of *Cinnamomum zeylanicum* is obtained from bark.

53. A method as claimed in claim 30 wherein the plant powder/extract of *Cuminum cyminum* is obtained from fruit.

54. A method as claimed in claim 30 wherein the plant powder/extract of *Carum carvi* is obtained from fruit.

55. A method as claimed in claim 30 wherein the plant powder/extract of *Cinnamomum camphora* is obtained from bark or leaves.

56. A method as claimed in claim 30 wherein the plant powder/extract of *Piper longum* is obtained from fruit or roots.

57. A method as claimed in claim 30 wherein the plant powder/extract of *Ocimum gratissimum* is obtained from leaves.

58. A method as claimed in claim 35 wherein the additive used is a binder selected from the group consisting of starch, starch paste, gum acacia, carboxy methylcellulose, Talc (Purified), Magnesium Stearate, Sodium Methyl Paraben and Sodium Propyl Paraben.

59. A method as claimed in claim 35 wherein the additive is a diluent comprising lactose.

60. A method as claimed in claim 35 wherein the additive used is a lubricant selected from the group consisting of starch and lactose.

61. A method as claimed in claim 30 wherein the mixture is mixed with a vehicle comprising 66.7% w/w sugar syrup.

* * * * *